(12) United States Patent
Perry

(10) Patent No.: US 8,217,049 B2
(45) Date of Patent: Jul. 10, 2012

(54) USE OF TYPE V PHOSPHODIESTERASE INHIBITORS IN THE TREATMENT OF EXERCISE INDUCED PULMONARY HEMORRHAGE IN THE EQUINE

(75) Inventor: Bryan J. Perry, West Seneca, NY (US)

(73) Assignee: ANOxA Corp., West Seneca, NY (US)

( * ) Notice: Subject to any disclaimer, the term of this patent is extended or adjusted under 35 U.S.C. 154(b) by 0 days.

(21) Appl. No.: 11/799,248

(22) Filed: May 1, 2007

(65) Prior Publication Data

US 2007/0254885 A1    Nov. 1, 2007

Related U.S. Application Data

(60) Provisional application No. 60/796,263, filed on May 1, 2006.

(51) Int. Cl.
  *C07D 471/04* (2006.01)
  *C07D 471/22* (2006.01)
  *C07D 487/04* (2006.01)
(52) U.S. Cl. .................. 514/257; 514/183; 514/256
(58) Field of Classification Search .................. 514/248
  See application file for complete search history.

(56) References Cited

U.S. PATENT DOCUMENTS 5,765,548 A * 6/1998 Perry .................. 128/200.24
2003/0070674 A1* 4/2003 Perry et al. ............. 128/200.14

OTHER PUBLICATIONS

Cohen et al., Inhibition of Cyclic 3'-5'-Guanosine Monophosphate-specific Phosphodiesterase Selectively Vasodilates the Pulmonary Circulation in Chronically Hypoxic Rats, 1996, J. Clin. Invest., vol. 97, No. 1, pp. 172-179.*
Rickards et al., Pulm Pharmacol Ther 2004, vol. 17, No. 3, p. 163-172.
Canadian Application No. 2,651,086—office action dated Dec. 16, 2010.

* cited by examiner

*Primary Examiner* — Jeffrey S. Lundgren
*Assistant Examiner* — Meghan Finn
(74) *Attorney, Agent, or Firm* — Michael F. Scalise

(57) ABSTRACT

The use of type V phosphodiesterase inhibitors as a novel independent therapeutic modality in the treatment of exercise induced pulmonary hemorrhage in equine is described. The type V phosphodiesterase inhibitor is injected into the horse intravenously as a stand-alone agent from about one-half hour to about seven (7) days prior to the onset of strenuous exercise.

10 Claims, No Drawings

USE OF TYPE V PHOSPHODIESTERASE INHIBITORS IN THE TREATMENT OF EXERCISE INDUCED PULMONARY HEMORRHAGE IN THE EQUINE

CROSS-REFERENCE TO RELATED APPLICATION

This application claims priority from U.S. provisional application Ser. No. 60/796,263, filed May 1, 2006.

BACKGROUND OF INVENTION

1. Field of the Invention

The present invention relates to the pulmonary hemodynamics of the equine. More particularly, this invention is directed to the use of type V phosphodiesterase inhibitors (PDIs) to reduce pulmonary capillary stress failure and, consequently, attenuation of exercise induced pulmonary hemorrhage (EIPH) in performance horses.

2. Prior Art

Horses experiencing EIPH, also known as "bleeders," represent a serious problem to the horse racing industry. Studies of horses in training and those in competition at racetracks have shown that from about 70% to 100% of them experience EIPH after performing. This has been shown both endoscopically (Pascoe et al. 1981; Sweeney, 1991) and from transtracheal washings (Whitwell and Greet, 1984). Horses that bleed heavily may have a reduced athletic performance and/or a shortened athletic career and thus EIPH is one of the most serious veterinary problems facing the horse racing industry.

Although numerous hypotheses have been proffered, it is generally accepted by the scientific community that pulmonary capillary stress failure is the casual determinant of exercise induced pulmonary hemorrhaging in performance horses. The rational is based on studies by M. Manohar (Am J. Vet. Res, 1993, 54:142-146) and West et al. (J. Appl. Physiol., 1991, 71:573-582 and J. Appl. Physiol 1993, 75: 1097-1109) among others who have demonstrated that excessive pulmonary artery pressure and stress failure at the pulmonary capillary level is due to increased transmural pressure during strenuous exercise of the equine. Further, it is known that horses have a relatively thin pulmonary blood-gas barrier to facilitate oxygen uptake during high intensity exercise. During exercise, pulmonary blood flow increases by as much as eight fold to satisfy the oxygen requirements of the horse. Basal compensatory mechanisms in mammals other than horses include functional recruitment of the pulmonary capillary bed.

Mills et al. (Br. Vet. J., 1996, 1952:119-122) studied the synthesis of nitric oxide (NO) in horses subjected to high speed treadmill tests by introducing N-nitro-L-arginine methyl ester (L-Name) directly into the pulmonary artery. This compound has been shown to inhibit the in situ production of NO, which is known to regulate resting pulmonary vascular tone in many species. During exercise a reduced level of NO in the lungs resulted in a significant increase in the pulmonary artery pressure. Conversely, the introduction of L-arginine, a structural analog of L-Name, into the pulmonary artery of exercising horses was shown by West et al. to reverse the restricted production of NO with a subsequent beneficial decrease in pulmonary artery pressure.

Even though the administration of L-arginine improves the production of NO in the lungs of equine and, consequently, results in less bleeding, there is still a need to further decrease pulmonary artery pressure during strenuous exercise of the equine. The present invention fulfills this need by the use of type V phosphodiesterase inhibitors as a novel independent therapeutic modality in the treatment of exercise induced pulmonary hemorrhage in equine.

SUMMARY OF INVENTION

Endogenous NO is continually produced throughout the various organ systems including the lungs of mammals. This starts with the amino acid L-arginine being converted via nitric oxide synthase to L-citruline and nitric oxide. Nitric oxide activates guanidylate cyclase to form cGMP (cyclic 3'5' guanine monophosphate), which results in selective (only acting on the lungs) pulmonary vasodilation via smooth muscle relaxation. The compound cGMP has a relatively short half-life of less than about 30 seconds and is rapidly degraded by the catalyst type V phosphodiesterases. However, in order to prevent pulmonary capillary stress failure, cGMP needs to be maintained throughout the duration of physical exercise to sustain smooth muscle relaxation. According to the present invention, this is accomplished by the intravenous injection of any one of a number of type V phosphodiesterase inhibitors in a prescribed dosage at a specified period prior to the onset of strenuous exercise.

The foregoing and additional objects, advantages, and characterizing features of the present invention will become increasingly more apparent upon a reading of the following detailed description together with the included drawings.

DETAILED DESCRIPTION OF THE PREFERRED EMBODIMENTS

According to the present invention, a type V phosphodiesterase inhibitor, and preferably (NA 1-(-6-chloro-4-(3,4-methylenedioxybenzyl)-aminoquinazolin-2-yl)-piperidine-4-carboxylate sesquihydrate (E4021), is given to a horse as a single agent in well defined concentrations. Type V phosphodiesterase inhibitor compounds will sustain the desired reduction in pulmonary artery pressure during maximum exercise for two hours and more. This methodology is based on accepting the premise of excessively high pulmonary vascular pressures of from about 100 mmHg to about 130 mmHg. Such high pulmonary vascular pressures are unique to equine during exercise and are a major contributor to the aberrant pulmonary transmural pressures that produce capillary stress failure, i.e. pressures greater than about 90 mmHg, resulting in subsequent pulmonary hemorrhage in the horse. Aberrant pulmonary transmural pressures are generally recognized as the underlying mechanism leading to EIPH in horses.

Previous attempts at using type V phosphodiesterase inhibitors to treat pulmonary capillary stress failure and EIPH also employed inhaled nitric oxide gas as an adjunct. This is described in U.S. Pat. No. 5,765,548 to Perry. Similarly, U.S. Pat. Nos. 5,823,180 and 5,570,683, both to Zapol, suggest using inhaled nitric oxide gas substrates in combination with type V phosphodiesterase inhibitors as a methodology to treat various pulmonary disorders in many kinds of mammals including equine.

However, the present invention demonstrates that when type V phosphodiesterase inhibitors, and preferably E4021, are administered as a single active agent, they selectively reduce pulmonary arterial pressure to less than about 80 mmHg in a strenuously exercising equine. This is premised on the occurrence of capillary stress failure resulting from excessively high transmural pulmonary artery pressure as the underlying mechanism leading to exercise induced pulmonary hemorrhaging in horses or the equine. Pulmonary capillary stress failure produces occult hemorrhaging into the lung/tracheobronchial tree. This hemorrhaging may be clinical as evidenced by obvious bleeding through the nostrils and mouth or sub-clinical as detected by endoscopic scoring in its presentation.

As a solution, the administration of a type V phosphodiesterase inhibitor in controlled doses to the horse is beneficial to obtund excessive pulmonary artery pressure with a corresponding reduction in pulmonary capillary stress failure. The type V phosphodiesterase inhibitor is administered by an intravenous injection prior to the onset of exercise. According to the present invention, type V phosphodiesterase inhibitors (PDIs) are selective stand-alone pulmonary vasodilators. In other words, there is no need for nitric oxide gas as an augmenting agent to the administered type V phosphodiesterase inhibitors. Suitable type V phosphodiesterase inhibitors include:

Tadalafil (C22H19N3O4)— (Cialis®), (6R-trans)-6-(1,3-benzodioxol-5-yl)-2,3,6,7,12,12a-hexahydro-2-methyl-pyrazino [1',2':1,6]pyrido[3,4-b]indole-1,4-dione.

Vardenafil (C23H32N6O4S)—(Levitra®), 4-[2-eyhoxy-5-(4-ethylpiperazin-1-yl) sulfonyl-phenyl]-9-methyl-7-propyl 3,5,6,8-tetrazabicyclo[4,3,0] none 3,7,9 trien-2-one.

E4010—4-(3-chloro-4-methoxybenzyl)amino-1-(4-hydroxypiperidino)-6-phthalazinecarbonitrile monohydrochloride.

E4021—(NA 1-(-6-chloro-4-(3,4-methylenedioxybenzyl)-aminoquinazolin-2-yl)-piperidine-4-carboxylate sesquihydrate. The latter compound is preferred.

For the purpose of reducing pulmonary capillary stress failure in a horse being subjected to a maximum level of exercise any one of the above type V phosphodiesterase inhibitors, and mixtures thereof, is administered to an equine by intravenous injection from about one-half hour to about one week, preferably about one hour, prior to the onset of exercise. Preferably, the compound is administered about one hour prior to exercise in a dosage ranging from about 5 μgram/kilogram of horse weight to about 200 μg/kg, preferably from about 10 μg/kg to about 100 μg/kg of horse weight.

The following example describes the use of type V phosphodiesterase inhibitors as a novel independent therapeutic modality in the treatment of exercise induced pulmonary hemorrhage in equine according to the present invention, and it sets forth the best mode contemplated by the inventors for carrying out the invention, but it is not to be construed as limiting.

EXAMPLE

Eight horses with previous evidence of EIPH were enrolled in the study. The candidate horses served as their own control and a predetermined rest period (no maximum exercise events) of one week was adhered to prior to initiation of the protocol. On initiation of the trial the subject horse received, prior to maximum exercise, either a dose of 10 μg/kg of weight of E4021 or a placebo. The eight horses were exercised in training/mock racing conditions at maximum intensity for greater than 1,000 meters followed by endoscopic exam/scoring about 60 to 90 minutes after the exercise event. Following exercise, the horses were examined with videoendoscopy for evidence of blood in the trachea about 60 minutes to 90 minutes after maximum exercise. The endoscope was passed to the level of the bifurcation of the trachea (carina) with images recorded on videotape. The subject horses were exercised a second time with a minimum rest period of one week between trials or as suggested by the collaborating veterinarian and/or trainer.

An objective scoring system (Pascoe et al. 1985) was used to indicate the presence or absence of EIPH, as well as its severity, if present. Zero indicates an absence of EIPH, and 1 to 4 indicated increasing amounts of blood observed endoscopically in the trachea. Scoring was done by the veterinarian conducting the examination, then later by another individual using the recorded examination. Because the veterinarian conducting the examination was by necessity directly involved in the project, a second scoring was conducted by an individual blinded to the treatment conditions.

The E4021 was administered from vials containing 50 mg of E4021/30 ml. The placebo was administered from 30 ml vials containing 0.9 W N saline. The baseline pre-intervention score represents a horse's score before administration of the first treatment consisting of either E4021 or the placebo. The Pl score was after placebo intervention and the post Tx Score was recorded after administration of E4021. The horses were then rested for at least one week without strenuous exercise before being subjected to a second exercise event. Those that first received the E4021 were then administered the placebo and visa versa.

The results are tabulated in Table 1 below.

TABLE 1

| Subject (Age) | Baseline Pre-Intervention | Pl | Post Tx |
|---|---|---|---|
| Horse 1 (7) | 3+ | 3+ | 3 |
| Horse 2 (5) | 3 | 3+ | 1 |
| Horse 3 (5) | N/A | 4+ | 2 |
| Horse 4 (9) | 4 | 4 | 0 |
| Horse 5 (14) | 4+ | 3+ | 3+ |
| Horse 6 (3) | 1 | 2 | 0 |
| Horse 7 (5) | 1+ | 1 | 0 |
| Horse 8 (5) | 4 | 2 | 2+ |

The subjects did not experience any untoward effects. Systemic hemodynamics (e.g. cardiac output, blood pressure) remained unchanged from controls and was within normal limits.

The conclusion is that the use of type V phosphodiesterase inhibitors, and particularly E4021, is a viable stand alone treatment agent for sustaining lung cellular cGMP (cyclic 3'5' guanine monophosphate) and, consequently, reducing the severity of exercise induced pulmonary hemorrhage in performance horses. The methodology is based on accepting the premise of excessively high pulmonary vascular pressures as a major contributor to the aberrant pulmonary transmural pressures that produce capillary stress failure and pulmonary hemorrhage. Evidence supports this conclusion as the underlying mechanism leading to EIPH in racehorses.

It is appreciated that various modifications to the inventive concepts described herein may be apparent to those of ordinary skill in the art without departing from the spirit and scope of the present invention as defined by the appended claims.

What is claimed is:

1. A method for reducing the severity of pulmonary hemorrhaging in a performance horse during an exercise event, the method consisting essentially of the steps of:
   a) providing a type V phosphodiesterase inhibitor;
   b) determining a physiological acceptable quantity of the type V phosphodiesterase inhibitor to reduce pulmonary arterial pressure to about 90 mmHg, or less during an exercise event that produces pulmonary vasculature pressures of greater than 90 mmHg;
   c) injecting the physiologically acceptable quantity of the type V phosphodiesterase inhibitor into the horse from about one-half hour to about 90 minutes prior to the exercise event; and d) wherein a nitric oxide gas is not co-administered.

2. The method of claim 1 including selecting the type V phosphodiesterase inhibitor from the group consisting of (6R-trans)-6-(1,3-benzodioxol-5-yl)-2,3,6,7,12,12a-hexahydro-2-methyl-pyrazino[1',2':1,6]pyrido[3,4-b]indole-1,4-dione, 4-[2-eyhoxy-5-(4-ethylpiperazin-1-yl)sulfonyl-phenyl]-9-methyl-7-propyl 3,5,6,8-tetrazabicyclo[4,3,0]none 3,7,9 trien-2-one, 4-(3-chloro-4-methoxybenzyl)amino-1-(4-hydroxypiperidino)-6-phthalazinecarbonitrile monohydrochloride, (NA 1-(-6-chloro-4-(3,4-methylenedioxybenzyl)-aminoquinazolin-2-yl)-piperidine-4-carboxylate sesquihydrate, and mixtures thereof.

3. The method of claim 1 including determining the physiological acceptable quantity of the type V phosphodiesterase inhibitor by first determining the horse's weight.

4. The method of claim 1 including injecting the type V phosphodiesterase inhibitor in a dosage ranging from about 5 µgram/kilogram to about 200 µg/kilogram of horse weight.

5. A method for sustaining the production of cyclic 3',5'-monophosphate in the lungs of a performance horse to reduce the severity of exercised induced pulmonary hemorrhaging during an exercise event, the method consisting essentially of the steps of:
   a) providing a type V phosphodiesterase inhibitor;
   b) determining, based on the horse's weight, a physiological acceptable quantity of the type V phosphodiesterase inhibitor to reduce pulmonary arterial pressure to about 90 mmHg, or less during an exercise event that produces pulmonary vasculature pressures of greater than 90 mmHg;
   c) injecting the physiologically acceptable quantity of the type V phosphodiesterase inhibitor into the horse from about one-half hour to about 90 minutes prior to the exercise event to thereby maintain arterial pressure in the lungs at less than 80 mmHg throughout the duration of the exercise event; and
   d) wherein a nitric oxide gas is not co-administered.

6. The method of claim 5 including selecting the type V phosphodiesterase inhibitor from the group consisting of (6R-trans)-6-(1,3-benzodioxol-5-yl)-2,3,6,7,12,12a-hexahydro-2-methyl-pyrazino [1',2':1,6]pyrido[3,4-b]indole-1,4-dione, 4-[2-eyhoxy-5-(4-ethylpiperazin-1-yl)sulfonyl-phenyl]-9-methyl-7-propyl 3,5,6,8-tetrazabicyclo[4,3,0]none 3,7,9 trien-2-one, 4-(3-chloro-4-methoxybenzyl)amino-1-(4-hydroxypiperidino)-6-phthalazinecarbonitrile monohydrochloride, (NA 1-(-6-chloro-4-(3,4-methylenedioxybenzyl)-aminoquinazolin-2-yl)-piperidine-4-carboxylate sesquihydrate, and mixtures thereof.

7. The method of claim 5 including injecting the type V phosphodiesterase inhibitor in a dosage ranging from about 5 µgram/kilogram of horse weight to about 200 µg/kg of horse weight.

8. A method for reducing the severity of exercised induced pulmonary hemorrhaging in a performance horse during an exercise event, the method consisting essentially of the steps of:
   a) providing (NA 1-(-6-chloro-4-(3,4-methylenedioxybenzyl)-aminoquinazolin-2-yl)-piperidine-4-carboxylate sesquihydrate as a type V phosphodiesterase inhibitor;
   b) determining a physiological acceptable quantity of the type V phosphodiesterase inhibitor to reduce pulmonary arterial pressure to about 90 mmHg, or less during an exercise event that produces pulmonary vasculature pressures greater than 90 mmHg;
   c) injecting the physiologically acceptable quantity of the type V phosphodiesterase inhibitor into the horse from about one-half hour to about 90 minutes prior to the exercise event to thereby maintain arterial pressure in the lungs at less than 80 mmHg throughout the duration of the exercise event; and
   d) wherein a nitric oxide gas is not co-administered.

9. The method of claim 8 including determining the physiological acceptable quantity of the type V phosphodiesterase inhibitor by first determining the horse's weight.

10. The method of claim 8 including injecting the type V phosphodiesterase inhibitor in a dosage ranging from about 5 µgram/kilogram of horse weight to about 200 µg/kg of horse weight.

* * * * *